United States Patent [19]

Fischell et al.

[11] Patent Number: 6,017,328
[45] Date of Patent: Jan. 25, 2000

[54] DEVICE FOR SUBCUTANEOUS MEDICATION DELIVERY

[75] Inventors: Robert E. Fischell, Dayton, Md.; David R. Fischell, Fair Haven, N.J.; Tim A. Fischell, Nashville, Tenn.

[73] Assignee: Magnolia Medical, LLC, Glenelg, Md.

[21] Appl. No.: 08/695,596

[22] Filed: Aug. 12, 1996

Related U.S. Application Data

[60] Division of application No. 08/173,983, Jan. 7, 1994, Pat. No. 5,545,143, which is a continuation-in-part of application No. 08/006,722, Jan. 21, 1993, abandoned.

[51] Int. Cl.[7] .................................................. A61M 5/178
[52] U.S. Cl. ........................ 604/180; 604/164; 604/506; 604/513
[58] Field of Search ..................................... 604/164, 167, 604/180, 264, 282, 280, 272, 523, 500, 502, 506, 513

[56] References Cited

U.S. PATENT DOCUMENTS

| | | |
|---|---|---|
| 2,288,323 | 4/1942 | Hollingsworth . |
| 3,030,953 | 4/1962 | Koehn . |
| 3,547,119 | 12/1970 | Hall et al. . |
| 3,683,911 | 8/1972 | McCormick . |
| 3,739,778 | 6/1973 | Monestere, Jr. et al. . |
| 3,853,127 | 12/1974 | Spademan . |
| 3,860,006 | 1/1975 | Bhupendra . |
| 3,919,724 | 11/1975 | Sanders et al. . |
| 4,040,427 | 8/1977 | Winnie . |
| 4,160,450 | 7/1979 | Doherty ............................. 128/214.4 |
| 4,235,234 | 11/1980 | Whitney et al. . |
| 4,311,137 | 1/1982 | Gerard . |
| 4,430,081 | 2/1984 | Timmermans . |
| 4,531,937 | 7/1985 | Yates . |
| 4,645,495 | 2/1987 | Vaillancourt . |
| 4,676,783 | 6/1987 | Jagger et al. ............................. 604/171 |
| 4,755,173 | 7/1988 | Konpk et al. . |
| 4,952,207 | 8/1990 | Lemieux ................................. 604/164 |
| 5,176,662 | 1/1993 | Bartholomew et al. . |

*Primary Examiner*—John D. Yasko

[57] ABSTRACT

The present invention is an injection port assembly for subcutaneous delivery of medication. A single molded body has a soft cannula extending downward from a generally flat bottom surface and a self-sealing septum mounted at the center of a top surface which is generally of a concave shape sloping downward towards its outer perimeter at which point the single body is very thin. The single body also has a tubular extension which is directed outward parallel to the skin's surface. A metal needle which penetrates through the septum and through the lumen of the soft cannula is used for inserting the cannula through the skin. Once the soft cannula is placed subcutaneously, the needle is removed and an adhesive tape is placed over the single body and onto the skin beyond the body's outer perimeter. By having a distal section of the needle which is smaller in diameter as compared to most of the needle's length, and by having the soft cannula fit tightly onto the needle, most of the cannula's length will be in tension during insertion thereby preventing an accordion-like compressional failure of the cannula. A quick-release connector on the proximal end of the tubular extension or mounted directly on the injection port assembly allows the tubing connecting the injection port assembly to a portable medication pump to be disconnected when the patient showers or performs some similar activity.

14 Claims, 14 Drawing Sheets

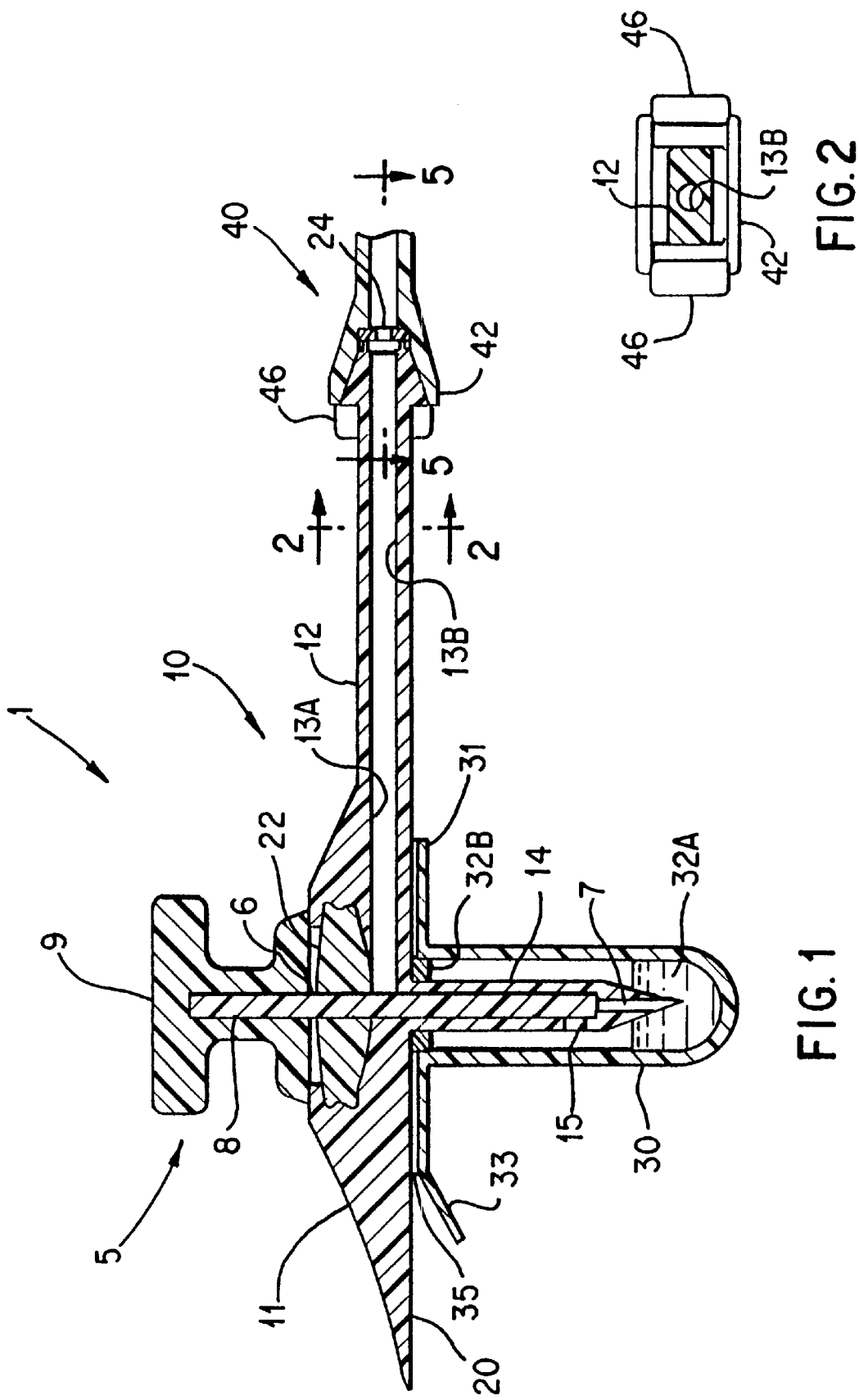

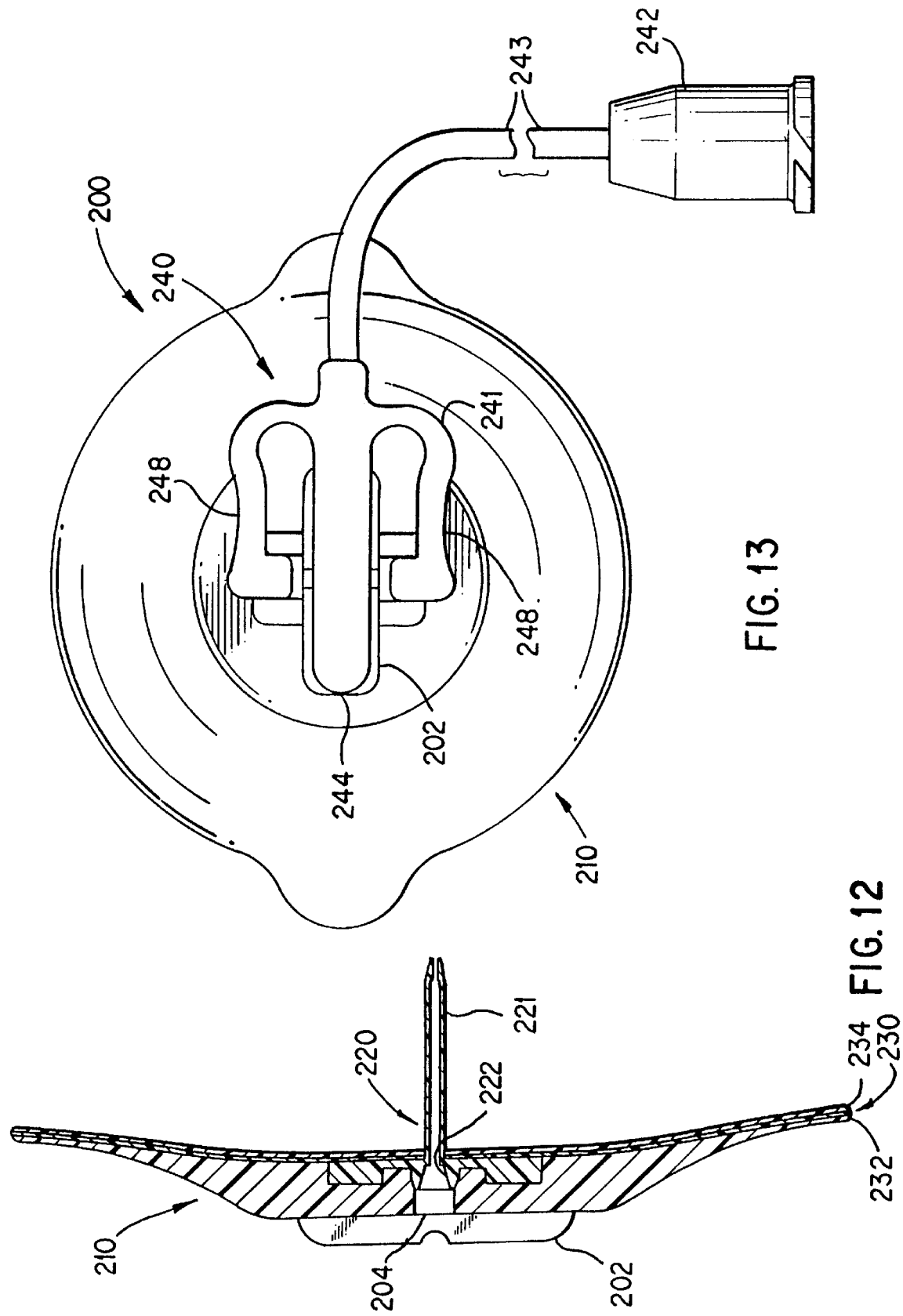

DEVICE FOR SUBCUTANEOUS MEDICATION DELIVERY

This is a divisional of application Ser. No. 08/173,983 filed on Jan. 7, 1994 now U.S. Pat. No. 5,545,143 which is a continuation-in-part application of U.S. patent application Ser. No. 08/006,722 filed Jan. 21, 1993 now abandoned.

FIELD OF USE

This invention is in the field of injection ports for subcutaneous delivery of medication.

BACKGROUND OF THE INVENTION

Subcutaneous injection is a standard method for the delivery of medication. To facilitate frequent or continuous subcutaneous injection of medication, subcutaneous injection ports are often used. Such injection ports extend through the skin and may remain in place for several days. Currently a major application of such injection ports is to provide chronic delivery of medication such as insulin from portable pumps. When used with a pump, a fluid line is required to connect the injection port to the portable pump. Another application of a subcutaneous injection port is to permit multiple injections without the need to repuncture the skin. In this application, medication is injected from a standard hypodermic syringe and needle through a soft elastomer septum into the injection port which delivers the medication subcutaneously.

If a hollow metal needle is left in place through the skin to provide medication delivery, after one or two days the needle becomes uncomfortable to the patient. To solve this problem, a disposable injection port was described in U.S. Pat. No. 3,547,119 by Hall et al which has a soft, thin-walled cannula which is subcutaneously inserted over a metal needle. After insertion, the metal needle is removed leaving only the soft cannula through the skin. However the Hall invention has several limitations, namely:

(1) it is designed for infusion into the bladder and not for subcutaneous injection;

(2) the soft, thin-walled cannula which is subcutaneously inserted over the metal needle is placed in compression during insertion which can result in buckling of the cannula;

(3) the device has an extremely high profile making it impractical for ambulatory use where it is highly desirable to be hidden under clothing; and (4) it does not provide a bacterial filter.

More recently, a soft cannula subcutaneous injection set described in U.S. Pat. No. 4,755,173 by Kanopka et al has become available. While being lower in profile than the Hall device and specifically designed for subcutaneous delivery of medication, the Kanopka invention also has several shortcomings, namely:

(1) there is no method for disconnecting the tubing near the point of subcutaneous insertion, thus requiring a long length of tubing to remain connected while showering, exercising or performing other activities for which having a long length of tubing is disadvantageous;

(2) many separate parts are required to construct the injection set which increases costs and the probability of leakage;

(3) like the Hall device, the soft, thin-walled cannula which is subcutaneously inserted over a hollow needle is placed in compression during insertion which can result in buckling of the cannula;

(4) the multiple parts design results in a comparatively high outward protrusion from the skin;

(5) there is a fluid chamber within the device which is a dead space for medication; and (6) the cylindrical segment of the catheter hub which extends below the holding pad presses on the skin and often becomes uncomfortable for the patient.

Another soft cannula subcutaneous injection port is described in U.S. Pat. No. 4,531,937 by Yates. The Yates device, however, has several disadvantages, namely:

(1) it requires a fluid trapping capability in the needle hub for the expulsion of air from the inside of the device;

(2) like the inventions by Hall and Kanopka, the soft, thin-walled cannula which is subcutaneously inserted over a hollow needle is placed in compression during insertion which can result in buckling of the cannula;

(3) it has a "stepped bore" diameter which forms a fluid chamber within the device which is a dead space for medication;

(4) it does not provide a bacterial filter; and (5) it lacks a flat surface for attachment to the skin to prevent bending of the soft cannula during prolonged insertion.

Still another soft cannula injection port is described in U.S. Pat. No. 4,311,137 by Gerard. The Gerard device, however, has several disadvantages, namely:

(1) it requires a complex movable needle/septum assembly with one position for flushing and a second position for insertion;

(2) it has a lumen (referred to as a passage) which forms a fluid chamber within the device which is a dead space for medication;

(3) it does not provide a bacterial filter;

(4) the Gerard design results in a comparatively high outward protrusion from the skin; and (5) like the inventions by Hall, Kanopka, and Yates, the soft, thin-walled cannula which is subcutaneously inserted over a hollow needle is placed in compression during insertion which can result in buckling of the cannula.

BRIEF SUMMARY OF THE PRESENT INVENTION

It is the goal of the present invention to overcome the several deficiencies of the prior art devices. Specifically, the present invention includes a quick-release connector which would typically be placed 5 to 10 cm from the device's main body. In another embodiment, the quick-release connector is placed directly onto the main body. Thus the soft cannula could remain in place through the skin while virtually all of the 100 plus cm of tubing connected to the portable pump could be temporarily detached and placed on a clean surface. When the main tubing is detached, a disposable sterilized cap can be placed over the quick-release connector to keep it sterile while showering, exercising or performing any other activity for which it is desirable to remove the long length of tubing. Furthermore, the connector can have a hard plastic needle which can penetrate through a previously slit septum on the injection port to provide a fluid path from an external portable pump, through the injection port and subcutaneously into the patient.

Another feature of the present invention is that an in-line bacterial filter can be incorporated into the device so that when the tubing is removed, a cap is not needed to prevent bacteria from entering the injection port. Such an in-line bacterial filter will, when dry, allow venting of air from the device and when wet (after priming) prohibit air bubbles from passing into the body. This is of particular importance for intravenous use.

Another feature of the present invention is a soft elastomer septum for hypodermic needle injection of medication via the device. This septum may be directly incorporated into the main body of the injection port or it can be contained in a quick-release connector which mates with the quick-release connector on the injection port.

Another important feature of the present invention is its one piece main body design which replaces five separate pieces and does not include a cylindrical segment extending below the bottom surface of the holding pad as required for the Kanopka et al invention. The one piece design reduces costs and further reduces the probability of a fluid leakage. The one piece design and the absence of a fluid chamber decreases the height of the device above the skin resulting in a desirable low profile which is more easily hidden under clothing. Still another novel feature of the present invention is a design in which the insertion needle and soft cannula cooperate to place the cannula in tension during insertion as opposed to compression, which compression can result in an accordion fold-up failure of the soft cannula. Another feature of the present invention is to allow soft cannula angles between 20 and 80 degrees relative to the bottom surface of the device which could be advantageous for intravenous insertion.

Another novel feature of the present invention is that the needle guard which is removed prior to placing the needle and cannula through the skin can contain a broad spectrum antibiotic substance such as an antibiotic ointment. Thus, when the needle guard is removed, some ointment remains on the needle which ointment can decrease infections at the insertion site and also can act as a lubricant for the exterior surface of the cannula.

Still another feature of the cannula is that it can be made with a side port which can allow continued delivery of medication even if the end port becomes blocked. Also, the side port allows for more diffuse infusion of the medication so that it would be taken up more quickly into the body.

Still another feature of the present invention is a concave upper surface of the single body which results in a flexible edge at the outside diameter of the main body. This is more comfortable for the patient because the flexible edge will more readily adapt to the changing shape of the skin surface.

Thus it is an object of this invention to have essentially a one piece main body for the subcutaneous delivery of medication thereby decreasing manufacturing cost and decreasing the probability of a fluid leak.

Another object of this invention is that the one piece main body allows a low profile above the skin.

Still another object of this invention is to provide a quick-release fluid connector in close proximity to the main body or directly connected onto the main body.

Still another object of this invention is that the removable connector include a hard plastic needle that penetrates through the same septum that is used for the insertion needle assembly.

Still another object of this invention is that the main body has a flexible outer edge.

Still another object of this invention is that the soft, flexible cannula and the insertion needle cooperate to have most of the length of the soft, flexible cannula in tension when it is being subcutaneously inserted.

Still another object of this invention is that the needle hub be constructed of solid materials and not contain a fluid trapping means.

Still another object of this invention is to provide a fluid exit side port near the distal end of the soft cannula.

Still another object of this invention is that an antibiotic substance can be placed within the needle guard so that needle and soft cannula lubrication is provided and also because of the antibiotic substance the probability of infection at the infusion site is minimized.

Still another object of this invention is to eliminate the creation of a fluid chamber dead space.

Still another object of this invention to provide an essentially flat bottom surface without any protrusion which would press on the skin.

Still another object of this invention is to provide an in-line bacterial filter that can prevent bacteria and/or air bubbles from passing into the patient.

Still another object of this invention is to allow connection through a flexible tube to a medication pump.

Still another object of this invention is to provide a soft elastomer septum for hypodermic injection of medication via the device.

Still another object of this invention is to separately mold a cannula section out of a comparatively hard plastic and insert it into a soft plastic main body whose great flexibility provides a more comfortable attachment to the skin.

These and other important objects and advantages of this invention will become apparent from the detailed description and drawings provided herein.

BRIEF DESCRIPTION OF THE DRAWINGS

FIG. 1 is a longitudinal cross section of the device shown in its form prior to insertion through the skin.

FIG. 2 is a transverse cross section of the device at section 2—2 of FIG. 1.

FIG. 12 is a cross section at 12—12 of the embodiment of the injection port shown in FIG. 10.

FIG. 13 is a top plan view showing a three-pronged connector mounted at the center of the injection port.

DETAILED DESCRIPTION OF THE DRAWINGS

Figure 3:
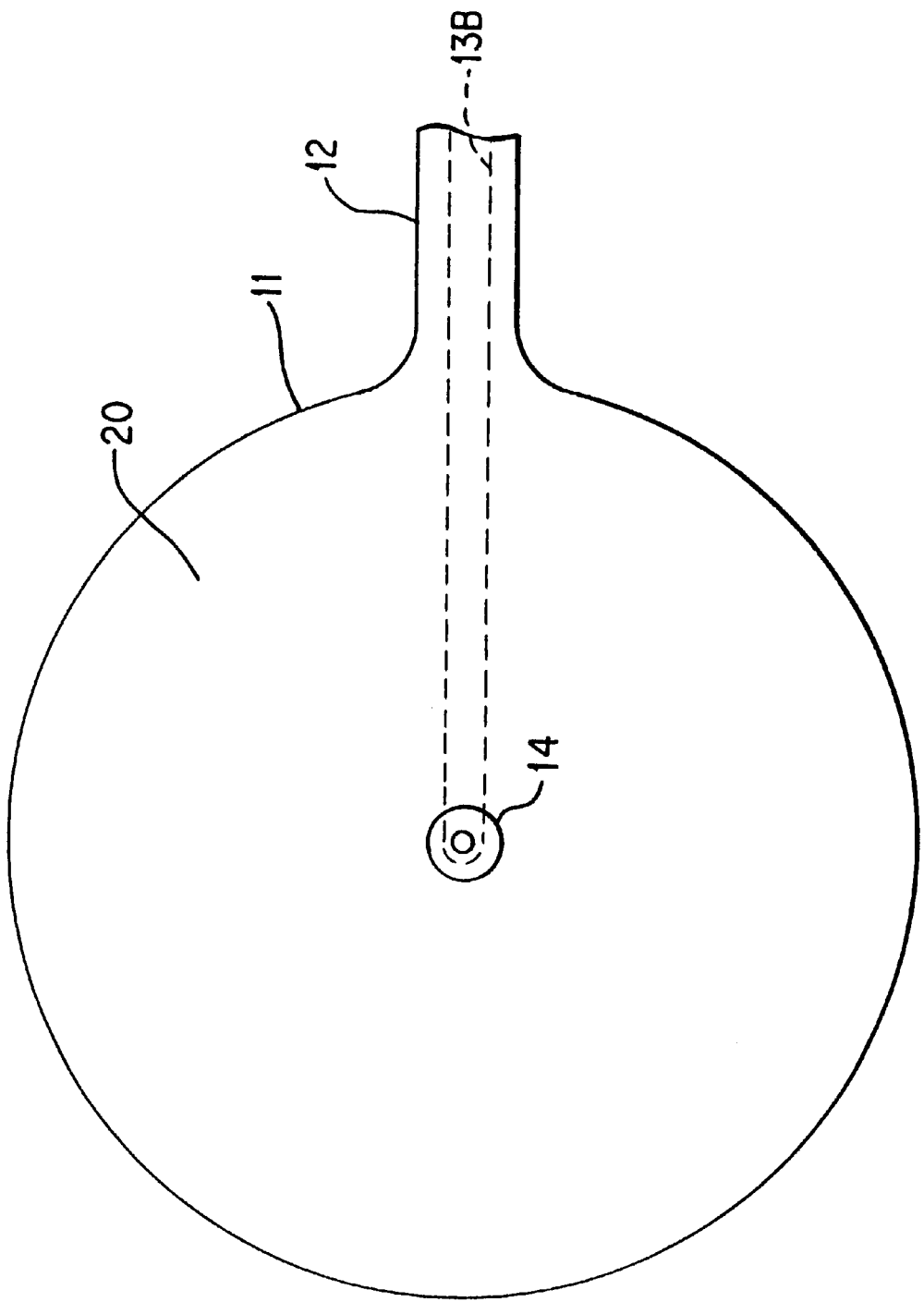
FIG. 3 shows the bottom of the device with the needle guard removed.

In FIG. 1 is shown a cross-sectional view of the present invention as it would appear immediately prior to insertion through the skin. The medication injection port system 1 consists of five subassemblies, namely: the insertion needle assembly 5, the injection port assembly 10, the needle guard 30, the quick-release connector assembly 40 and the cap assembly 50 (shown in FIG. 6). The needle assembly 5 consists of a solid core needle 6 having a proximal section 8 and a reduced diameter distal section 7 and a rigid plastic handle 9. The needle 6 could also be entirely or partially hollow and would typically be made from a stainless steel such as type 304. The diameter of the needle would typically be 0.45 mm except for the distal section 7 which would typically be 0.25 mm.

The injection port assembly 10 consists of a one piece main body 11 having a tubular body extension 12, an inlet lumen 13A, a tubular lumen 13B and a soft, flexible cannula 14 having a side port 15. Although it is ideal to have the body extension 12 and the soft cannula 14 molded into the main body 11, the present invention also envisions either one of these two parts to be formed separately and then bonded or adhesively joined into the main body 11. A removable needle guard 30 which is temporarily attached to the bottom surface 20 of the main body 11 protects the patient from being inadvertently stuck by the needle's sharp end prior to insertion through the skin. The needle guard 30 is shown with a thin, flexible flange 31 that has a tab 33 which extends beyond the perimeter of the flange 31 at one place on the flange's perimeter. A pressure sensitive adhesive coating 35 placed on the upper surface of the flange 31 holds onto the bottom surface 20 until the tab 33 is used to pull the flange 31 and needle guard 30 away from the main body 11. It is also envisioned that the adhesive could be placed on the bottom surface 20 of the body 11 where it would adhere to the skin after the needle guard is removed.

Within the needle guard 30 there can be placed an antibiotic ointment either at site 32B if it is desired that the ointment only cover the insertion puncture wound after insertion, or the ointment can be placed at position 32A if it is also desired to lubricate and coat the exterior surface of the cannula as it is inserted through the subcutaneous tissue. It should be noted that there is a closed, air tight volume within the needle guard 30 that would prevent drying out of an antibiotic ointment prior to the needle guard's removal from the bottom surface of the main body 11. It should also be noted that the shipping package which is used to sterilize and ship the injection port assembly could also have molded into it a needle guard section which could also include an antibiotic ointment.

Also shown in FIG. 1 is a self-sealing, soft, elastomer septum 22 which seals the fluid lines after the needle 6 is pulled out. The septum 22 would typically be fabricated from a low durometer silicone rubber that has been placed in compression.

Figure 5:
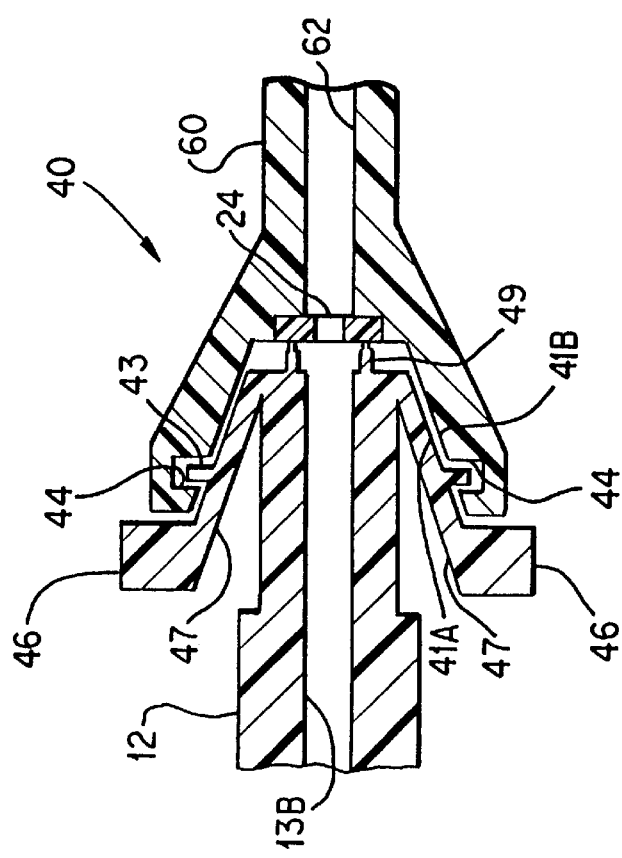
FIG. 5 shows an enlarged cross section of the quick-release connector at section 5—5 of FIG. 1.

FIG. 2 shows the transverse cross section of the tubular body extension 12 which encloses the lumen 13B. The connector housing 42 and quick-release actuator buttons 46 are shown in FIGS. 1 and 2. The tubular extension 12 terminates in a quick-release connector 40 which is also illustrated in FIG. 5. FIGS. 1 and 5 show a soft elastomer seal 24 within the quick-release connector 40 which provides a fluid tight seal.

Before insertion of the injection port system 1 into the skin, the guard 30 is removed. When this is accomplished, the view of the bottom of the injection port assembly 10 would be as shown in FIG. 3. After the guard 30 is removed, the patient would grip the needle assembly handle 9 and push it and the soft cannula 14 through the skin. When doing this, the exterior shoulder of the needle (where proximal section 8 joins distal section 7) cooperates with the interior shoulder of the cannula 14 to place most of the length of the cannula 14 in tension. This design prevents the soft, flexible cannula 14 from folding up like an accordion (i.e., buckling) when it is pushed through the skin.

Figure 4:
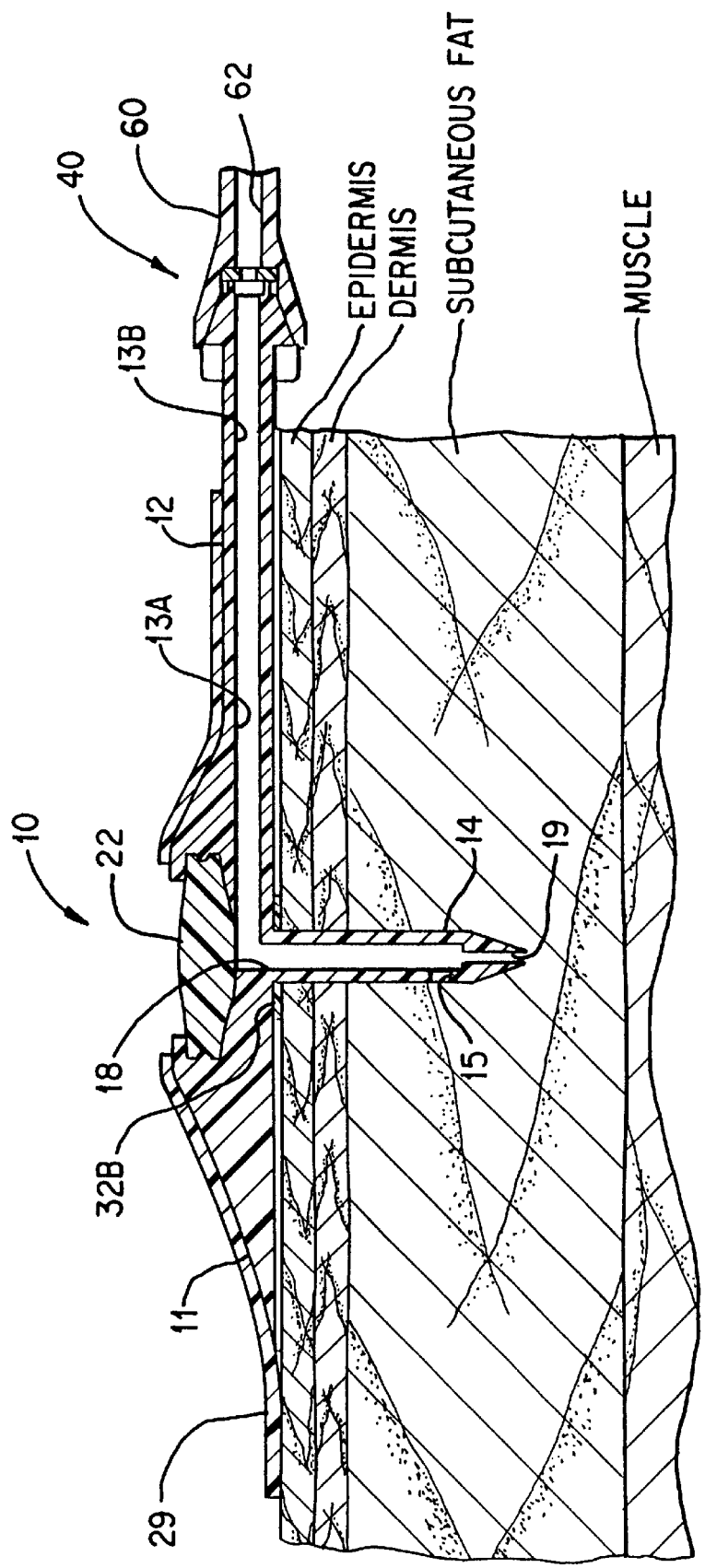
FIG. 4 is a longitudinal cross section of the injection port and body tubular extension showing how the soft, flexible cannula is subcutaneously inserted into the subcutaneous fat.

FIG. 4 shows the injection port assembly 10 with the needle assembly 5 removed and the soft cannula 14 in place with its distal end lying in the subcutaneous fat. Also shown in FIG. 4 is the quick-release connector 40 whose female connector is joined to the distal end of the tubing 60 and whose proximal end is connected to a portable pump (not shown). Thus the liquid medication coming out of the pump first passes through the lumen 62 of the tubing 60, then the lumen 13B of the tubular body extension 12, then through the inlet lumen 13A of the main body 11, then through the exit lumen 18 of the flexible cannula 14 and finally out the end hole 19 of the cannula 14 and/or through the cannula's side port 15. It should be understood that the side port 15 could be omitted. Conversely, the end hole 19 could be replaced by a sharpened point and only the side hole(s) 15 could be used. Also, the tubular body extension 12 could be formed from a separate piece of plastic and then joined with a fluid tight seal into the body 11. It should be noted that there is an absolutely no fluid chamber within the main body 11. This is a result of the bottom surface of the septum 22 being placed at the proximal end of the exit lumen 18. There are only the continuous lumens 13A, 13B and 18 through which the medication flows. Therefore there is not the disadvantage of having a fluid chamber dead space which increases the height of the main body and in which medication such as insulin could precipitate out as solid insulin. In this embodiment, the lumens 13A and 13B are the connecting lumens between the quick-release connector assembly 40 and the exit lumen 18 in the soft cannula 14.

It should be noted that the upper surface of the main body 14 is concave. This shape maximizes the flexibility of the outer perimeter of the main body 11. This provides for more patient comfort because where the main body perimeter joins onto the skin, it will more readily follow a changing shape of the skin surface. FIG. 4 also shows an adhesive tape 29 which extends for approximately 6 mm beyond the outer perimeter of the main body 11. This tape would also follow the skin's changing shape. The FIG. 4 embodiment does not use an adhesive on the bottom surface of the main body 11, however such an adhesive could be used instead of or in combination with the adhesive tape 29 to hold the main body 11 against the patient's skin.

FIG. 4 also shows a flat surface on the bottom of the main body 11. This is in contradistinction to the Yates invention which shows no flat surface at all and the Kanopka et al invention which requires a cylindrical segment extending below the bottom surface of a holding pad into which cylindrical segment the soft cannula is inserted. Although there may be some advantages to a cylindrical segment extending below the bottom surface of Kanopka's "holding pad", such a cylindrical segment protruding into the skin for several days can be uncomfortable for some patients. The flat surface at the bottom of the main body 11 should be more comfortable for long term use for most patients.

FIG. 5 shows a view of the quick-release connector assembly 40 which is orthogonal to the views shown in FIGS. 1 and 4. The tubular extension 12 has at its proximal end a tapered male portion in the form of a flat top pyramid with two broad sides and two narrow sides. The broad sides lie generally parallel to the skin while the two narrow sides are perpendicular to the skin surface. This is also true for the tubular extension 12 whose broad surfaces lie parallel to the skin and whose narrow surfaces lie perpendicular to the skin. This geometry makes it easy for the patient to bend the tubular extension upward away from the skin in order to easily squeeze the actuator buttons 46 of the quick-release connector 40. This geometry also places the quick-release actuator buttons 46 in an orientation where they cannot be inadvertently released by pushing down on the skin at the site of the quick-release connector. It should be understood that a cylindrical tubular extension would also be satisfactory.

Figure 7:
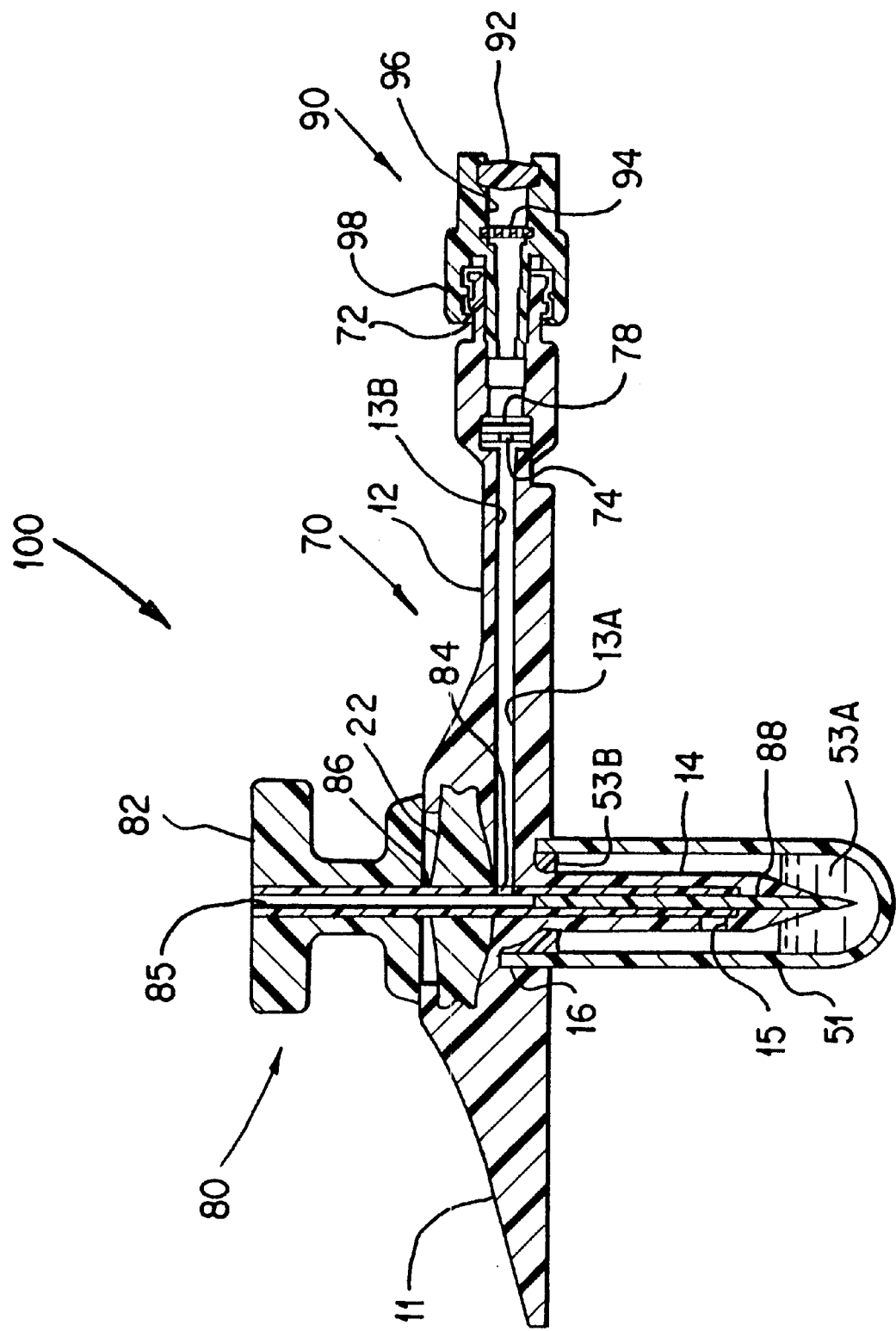
FIG. 7 is a longitudinal cross section of an alternate embodiment of the device shown in its form prior to insertion through the skin which embodiment shows a bacterial filter, a mini-Luer lock fitting for quick-release, a hollow upper tube insertion needle and a soft elastomer septum at the proximal end of the quick-release fitting for hypodermic injection of medication via the device.

Returning now to FIG. 5 we see that the male portion has a taper 41A which mates with the taper 41 of the female portion of the quick-release connector 40. Each actuator button 46 is mounted on a flexure 47 which also has the male detent 43 mounted on its exterior surface. When the female detent 44 is mated with the male detent 43, the quick-release connector 40 has its two portions firmly joined together with the circular ridge 49 making a fluid tight juncture with the elastomer washer 24. When the index finger and thumb are placed on and squeezed together onto the actuator buttons 46, the quick-release connector 40 can be easily separated by pulling outward on the tubing 60. For reconnection, the tubular extension 12 and the tubing 60 are pushed together until the detents 43 and 44 are joined. If the male and female portions of the quick-release connector 40 are rotated by 180 degrees, the male detents 43 will still snap into the female detents 44. Thus, the patient need not be aware of the angular orientation of the tubular extension 12 relative to the tubing 60 other than the fact that the broad sides of the male and female portions must be aligned. Alternatively, a Luer lock fitting, especially a miniature version as shown in FIG. 7, could accomplish the same function as the quick-release connector 40.

Figure 6:
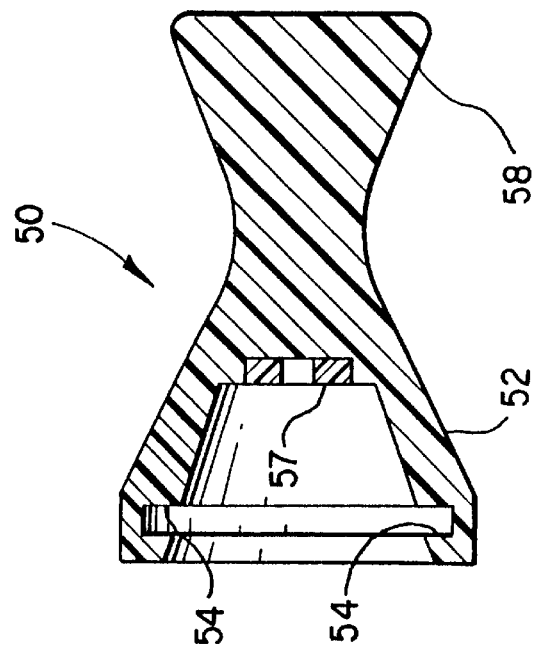
FIG. 6 shows an end cap.

When the female portion of the connector 40 and the tubing 60 are disconnected from the male portion, a sterilized disposable female cap 50 shown in FIG. 6 can be placed over the male portion. The female detents 54 would then mate with the male detents 43, and the circular ridge 49 would seal against the soft elastomer seal 57. The handle 58 on the cap 50 makes for easy assembly with the male portion of the quick-release connector 40. If desired, a properly configured male plug (not shown) could be used to close off the female portion of the quick-release connector 40 when the male and female portions are separated. It should be understood that the cap 50 would be used to maintain sterility when showering, swimming or performing any other activity which would be enhanced by disconnecting the tubing 60 and the portable medication pump from the main body assembly 10. To reconnect the pump, the female cap 50 is removed and the quick-release connector 40 is reconnected.

The main body 11 and needle handle 9 would typically be molded from Teflon, Surlyn, polyurethane or any similar plastic which is readily formed by injection molding. The tubing 60 could be formed with an interior cylinder (not shown) of polyolefin or a similar plastic and an outer tubing (not shown) of PVC or a similar plastic. It is important that all surfaces in contact with the medication do not degrade that medication.

It should also be noted that the lengths of the needle 6 (including the distal portion 7) and the cannula 14 could be varied in order to accommodate individuals with different thicknesses of subcutaneous fat. For example, a soft cannula length of 8.5 mm below the bottom surface 20 of the body 11 could be used for most individuals. For pediatric use or for very thin individuals, one-quarter to two-thirds that length would be appropriate. For individuals with a thicker fat layer, or for suprapubic or intravenous use, an increased length of soft cannula could be used.

It is also envisioned to coat the exterior surface of the cannula 14 with a lubricity coating to aid in its insertion through the skin.

In FIG. 7 is shown a cross-sectional view of an alternate embodiment of the present invention as it would appear immediately prior to insertion through the skin. The medication injection port system 100 consists of four subassemblies, namely: the needle guard 51, the insertion needle assembly 80, the injection port assembly 70 and the mini-Luer-lock connector assembly 90. The needle assembly 80 consists of a hollow tube proximal section 86 and a reduced diameter solid needle distal section 88. A proximal portion of the proximal section 86 is fixedly attached to a comparatively rigid plastic handle 82. The tube 86 has an inlet port 84 which allows the passage of fluid from the inlet lumen 13A into the lumen 85 of the tube 86. Fluid entering the lumen 85 will flow out of the top opening of the needle's proximal section 86. This allows the fluid passageways in the injection port system 100 to be flushed out or primed (i.e., have air removed from the lines) either prior to or after subcutaneous insertion of the soft cannula 14. Both the hollow and the solid sections of the needle would typically be made from a stainless steel such as type 304. The outside diameter of the proximal section 86 would typically be 0.45 mm and the diameter of the distal section 88 would typically be 0.25 mm.

The injection port assembly 70 consists of a one piece main body 11 having a (typically) flat tubular body extension 12 with a lumen 13B which is in fluid communication with the inlet lumen 13A and the exit lumen of the soft cannula 14 having a side port 15. Although it is ideal to have the body extension 12 and the soft cannula 14 molded into the main body 11, the present invention also envisions either one of these two parts to be formed separately and then bonded or adhesively joined into the main body 11. A removable needle guard 51 which fits into a groove 16 of the main body 11 protects the patient from being inadvertently stuck by the needle's sharp end prior to insertion through the skin. Within the needle guard 51 there can be placed an antibiotic ointment either at site 53B if it is desired that the ointment only cover the insertion puncture wound after insertion, or the ointment can be placed at position 53A if it is also desired to lubricate and coat the exterior surface of the cannula as it is inserted through the subcutaneous tissue. Also shown in FIG. 7 is a self-sealing, soft, elastomer septum 22 which seals the fluid lines after the insertion needle assembly 80 is pulled out. The septum 22 would typically be fabricated from a low durometer silicone rubber that has been placed in compression.

A bacterial filter 78 is placed in the fluid path within the injection port 70 to prevent the delivery of bacteria into the subcutaneous tissue. Such a bacterial filter 78 is shown as part of the mini-Luer lock fitting 72 attached to the injection port 70. A filter support disk 74 provides structural support for the bacterial filter 78 while allowing free passage of fluid into the lumen 13B.

The mini-Luer lock connector assembly 90 consists of a male miniature Luer lock fitting containing a soft, self-sealing elastomer injection septum 92 through which hypodermic needles can be inserted to inject medication from a syringe. A needle stop 94 with holes too small in diameter for a needle to penetrate prevents the hypodermic needle from damaging the bacterial filter 78. Because of the needle stop 94, fluid from a hypodermic needle syringe will be injected into the lumen 96, pass through the needle stop 94 then through the bacterial filter 78 into the main body of the injection port 70. The injection septum 92 would typically be fabricated from a low durometer silicone rubber that has been placed in compression. The connector assembly 90 would typically be located between 5 and 10 cm from the needle assembly 80; and would always be less than 25 cm away. Most typically, the connector 90 would be located at a position from the edge of the main body 11 within a distance that is less than the diameter of the main body 11.

Although FIG. 7 shows an injection septum 92 at the end of the mini-Luer lock assembly 90, it is understood that, as in FIG. 1, this connector could instead attach to a length of flexible tubing for connection to an external, portable medication pump.

Figure 8:
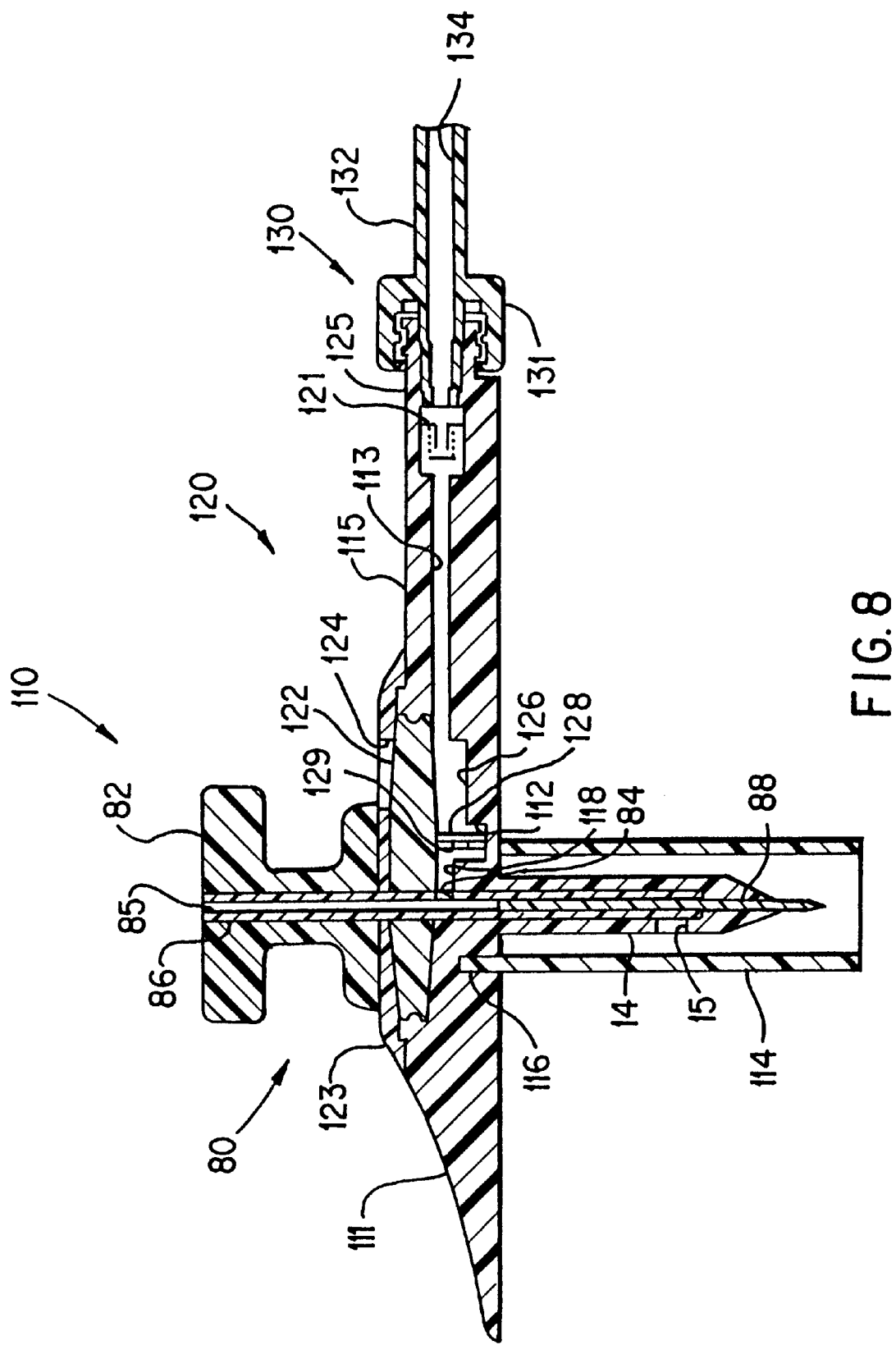
FIG. 8 is a longitudinal cross section of still another embodiment of the device shown in its form prior to insertion through the skin. This embodiment contains a bacterial filter, and both a means for hypodermic injection as well as delivery of medication from an external, portable pump.

In FIG. 8 is shown a cross-sectional view of still another embodiment of the present invention as it would appear immediately prior to insertion through the skin. The medication injection port system 110 consists of four subassemblies, namely: the insertion needle assembly 80, the needle guard 114, the injection port assembly 120 and the mini-Luer-lock connector assembly 130. The needle assembly 80 consists of a hollow tube 86 having a reduced diameter solid needle 88 inserted into its distal end and a comparatively rigid plastic handle 82. The tube 86 has an inlet port 84 which allows the passage of fluid from the lumen 113 into the lumen 85 of the tube 86. Fluid entering the lumen 85 will flow out of the top of the tube 86. This allows the fluid passageways in the injection port system 110 to be flushed out or primed; i.e., medication displaces the air in the fluid lines. The tube 86 and solid needle 88 would typically be made from a stainless steel such as type 304. The outer diameter of the tube 86 would typically be 0.45 mm and the diameter of the needle 88 would typically be 0.25 cm.

The injection port assembly 120 consists of a one piece main body 111 having a flat tubular body extension 115 with a lumen 113 and a soft, flexible cannula 14 having a side port 15. Although it is ideal to have the body extension 115 and the soft cannula 14 molded into the main body 111, this and other embodiments envision either one of these two parts to be formed separately and then bonded or adhesively joined into the main body 111. A removable needle guard 114 which fits into a groove 116 of the main body 111 protects the patient from being inadvertently stuck by the needle's sharp end prior to insertion through the skin. Also shown in FIG. 8 is a self-sealing, soft, elastomer septum 122 which is placed in compression by a septum cap 123. The septum 122 seals the fluid lines after the insertion needle assembly 80 is pulled out. The septum 122 would typically be fabricated from a low durometer silicone rubber that has been placed in compression. Above the septum 122 is an injection hole 124 in the septum cap 123. Below the septum 122 and in line with the injection hole 124, is an injection chamber 126 which is in fluid communication with the bacterial filter chamber 112 on one side and the lumen 113 on the other. After subcutaneous insertion and then removal of the needle assembly 80, the bacterial filter chamber 112 connects through the main body connecting lumen 118 to the exit lumen of the soft cannula 14.

To prevent the delivery of bacteria into the patient's body, a bacterial filter 128 is placed in the fluid path between the injection chamber 126 and the exit lumen of the soft cannula 14 through which medication is delivered into the patient. A filter support disk 129 provides structural support for the bacterial filter 128 while allowing free passage of fluid into the exit lumen of the soft cannula 14. A check valve 121 is located between the mini-Luer lock connector 125 and the injection chamber 126. After subcutaneous insertion of the cannula 14 and removal of the needle assembly 80, medication delivered by a hypodermic syringe through the septum 122 into the injection chamber 126 will flow through the bacterial filter 128 into the connecting lumen 118, through the exit lumen in the soft cannula 14 and into the patient's body because the check valve 121 prevents flow out through the lumen 134.

The mini-Luer lock connector assembly 130 consists of a male miniature Luer lock fitting 131 which connects to a length of flexible tubing 132 with lumen 134 which would connect to an external fluid pumping device. Medication from a pump would flow through the lumen 134 in the flexible tube 132, through the check valve 121 into the lumen 113 in the flat tubular body extension 115 of the one piece main body 111, then through the injection chamber 126 through the bacterial filter 128, filter support disk 129, and lumen 118 into the exit lumen of the soft cannula 14 and then into the patient's body.

Figure 9:
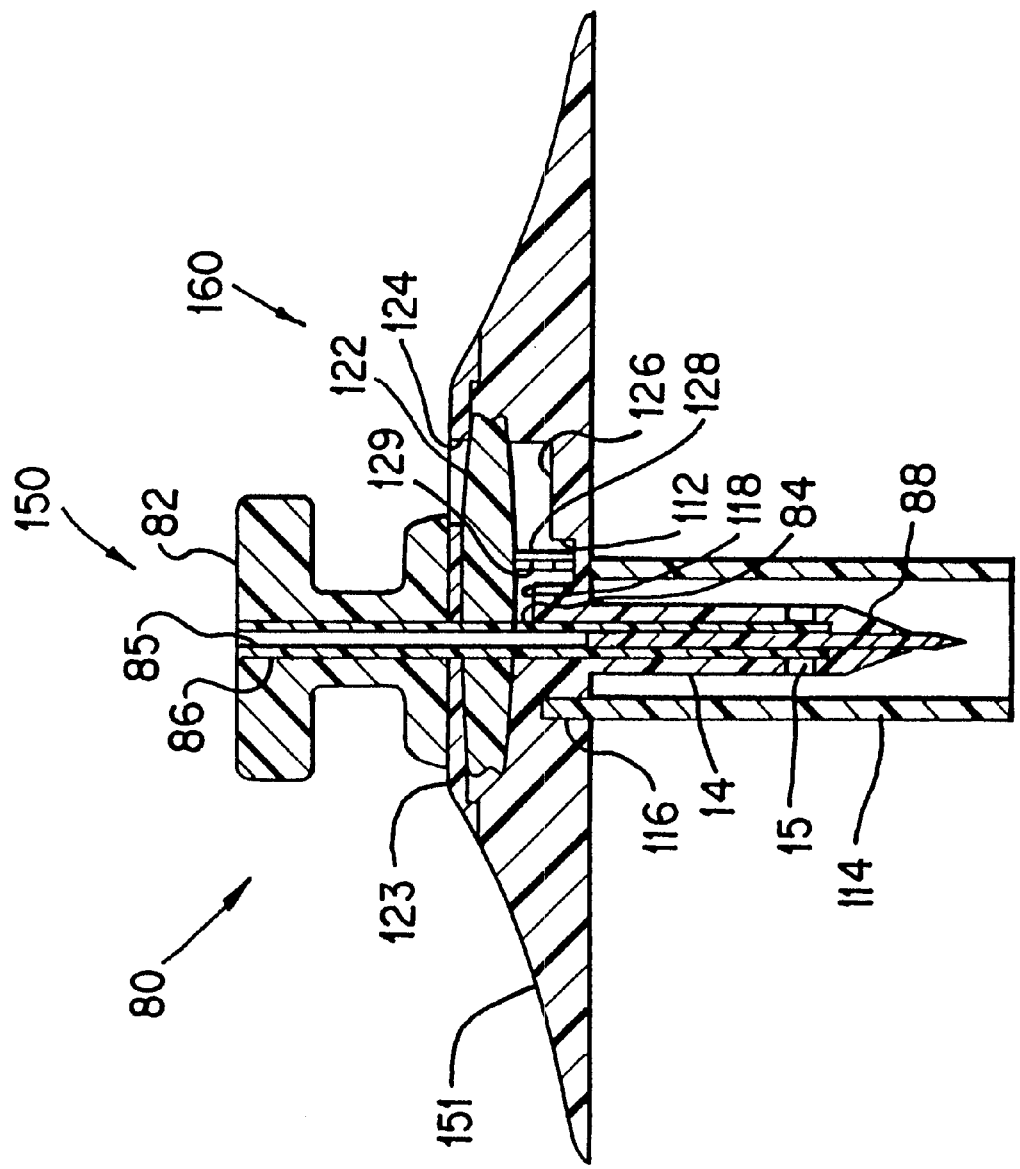
FIG. 9 is a longitudinal cross section of yet another embodiment of the device shown in its form prior to insertion through the skin. This embodiment contains a bacterial filter, and only a means for hypodermic injection of medication.

In FIG. 9 is shown a cross-sectional view of yet another embodiment of the present invention as it would appear immediately prior to insertion through the skin. The medication injection port system 150 consists of three subassemblies, namely: the insertion needle assembly 80, the needle guard 114 and the injection port assembly 160. The needle assembly 80 consists of a hollow tube 86 having a reduced diameter solid needle 88 inserted into its distal end and a plastic handle 82. The tube 86 has an inlet port 84 which allows the passage of fluid from the lumen 126 into the lumen 85 of the tube 86. Fluid entering the lumen 85 will flow out of the top exit port of the tube 86. This allows the fluid passageways in the injection port system 150 to be flushed or primed.

The injection port assembly 160 consists of a one piece main body 151 having a soft, flexible cannula 14 which has two side ports 15. Although it is ideal to have the soft cannula 14 molded into the main body 151, the present invention also envisions either one of these two parts to be molded separately and then bonded or adhesively joined into the main body 151. A removable needle guard 114 which fits into a groove 116 of the main body 151 protects the patient from being inadvertently stuck by the, needle's sharp end prior to insertion through the skin. Also shown in FIG. 9 is a self-sealing, soft, elastomer septum 122 which is placed in compression by a septum cap 123. The septum 122 seals the fluid lines and chambers after the insertion needle assembly 80 is pulled out. The septum 122 would typically be fabricated from a low durometer silicone rubber that has been placed in compression. Above the septum 122 is an injection hole 124 in the septum cap 123. Below the septum 122 and in line with the injection hole 124, is an injection chamber 126 which is in fluid communication with the bacterial filter chamber 112.

A bacterial filter 128 to prevent the delivery of bacteria into the patient's body is placed in the fluid path within the injection port 160 between the injection chamber 126 and the exit lumen of the soft cannula 14 which delivers medication to the patient. A filter support disk 129 provides structural support for the bacterial filter 128 while allowing free passage of fluid into the exit lumen of the soft cannula 14. After subcutaneous insertion of the cannula 14 and removal of the needle assembly 80, medication delivered by a hypodermic syringe through the septum 122 into the injection chamber 126 will flow through the bacterial filter 128 into the connecting lumen 118 and through the exit lumen in the soft cannula 14 and into the patient's body.

Although FIG. 7, 8 and 9 show vertically oriented, disk-shaped bacterial filters, it is understood that the shape of the filter might be cylindrical, or rectangular and the orientation could be at any angle.

Although FIGS. 1, 4, 7, 8 and 9 show a flexible cannula 14 which is generally perpendicular to the bottom surface 17 of the main body, it should be understood that there could be conditions which would require the cannula 14 to be inclined at an angle between 20 and 80 degrees relative to the bottom surface 17. Such angles could be advantageous for intravenous insertion of the cannula 14.

Although FIG. 8 shows a check valve 121 to prevent flow out of the mini-Luer lock connector 130 during hypodermic injection, it is clear that alternate means for preventing such flow such as a closed mini-Luer cap could be used to prevent such flow.

Figure 10:
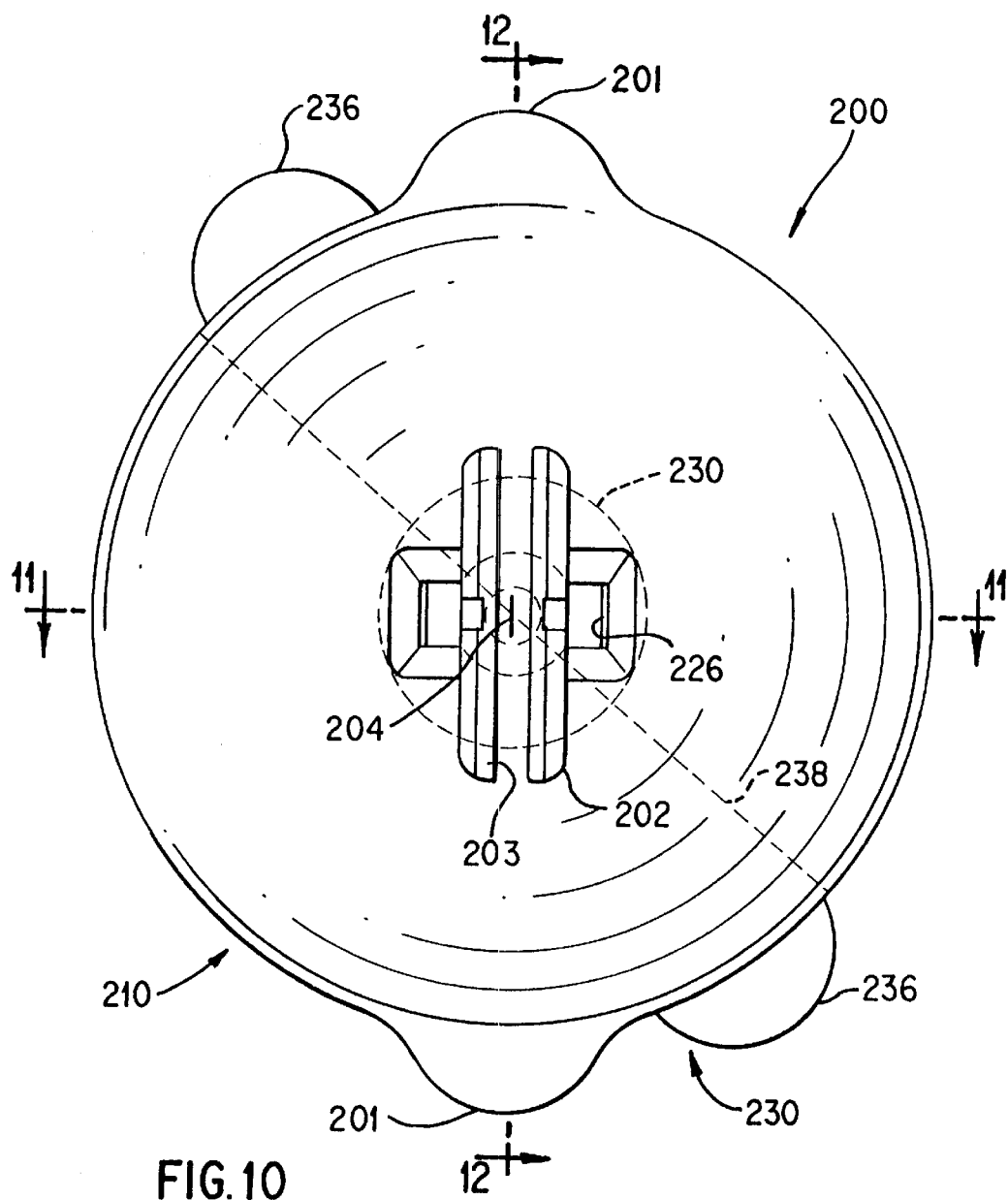
FIG. 10 is a top plan view of another embodiment of an injection port.
Figure 11:
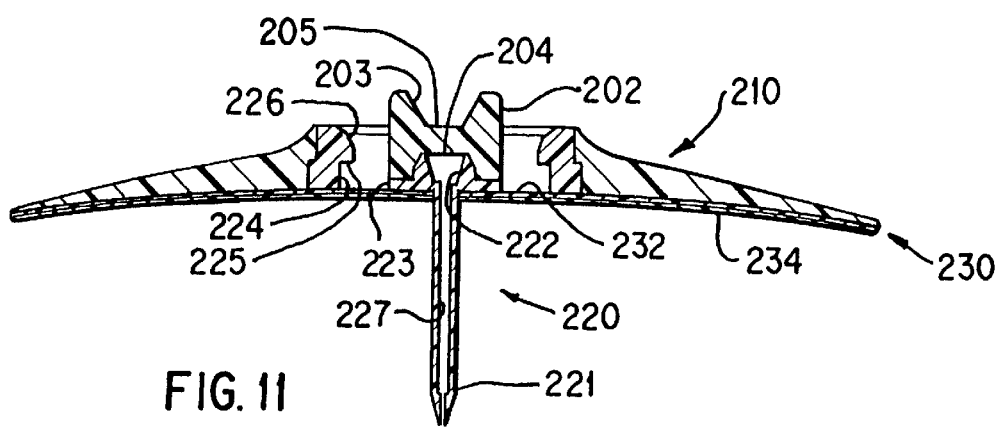
FIG. 11 is a cross section at 11—11 of the embodiment of the injection port shown in FIG. 10.

FIGS. 10, 11 and 12 illustrate another embodiment of an injection port assembly 200 which consists of three sub-assemblies, namely: a main body 210, a cannula section 220 and an adhesive assembly 230. The main body 210 is generally in the form of a flat, circular disk. Two projections 201 are aligned in the direction of the guide ridges 202. The interior surface 203 of the guide ridges 202 are used to help guide the plastic needle 245 (shown in FIGS. 15 and 16) into the slit 204 of the septum 205 which is located at the center of the ridges 202 which is also the center of the main body 210. The projections 201 aid the patient in aligning the injection port assembly 200 in a generally horizontal direction when adhesively attaching it to the skin in the abdominal region. When the ridges 202 are in a horizontal position, it is somewhat easier for the patient to slide the plastic needle 245 into its proper place inside the ridges 202 and into the slit 204.

Figure 15:
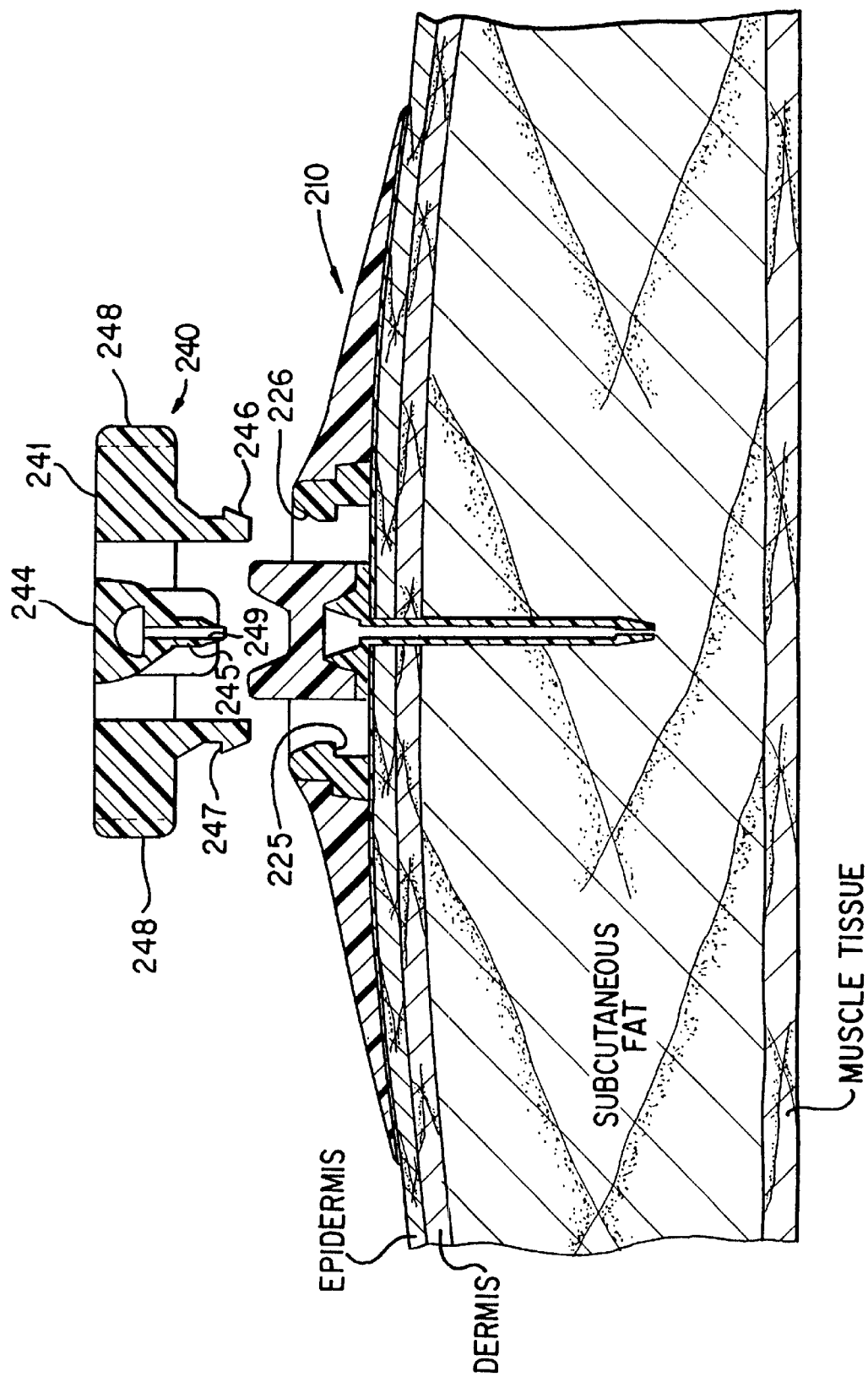
FIG. 15 is a cross section of the three-pronged connector and the injection port showing the needle assembly removed and the three-pronged connector above the top surface of the injection port.
Figure 16:
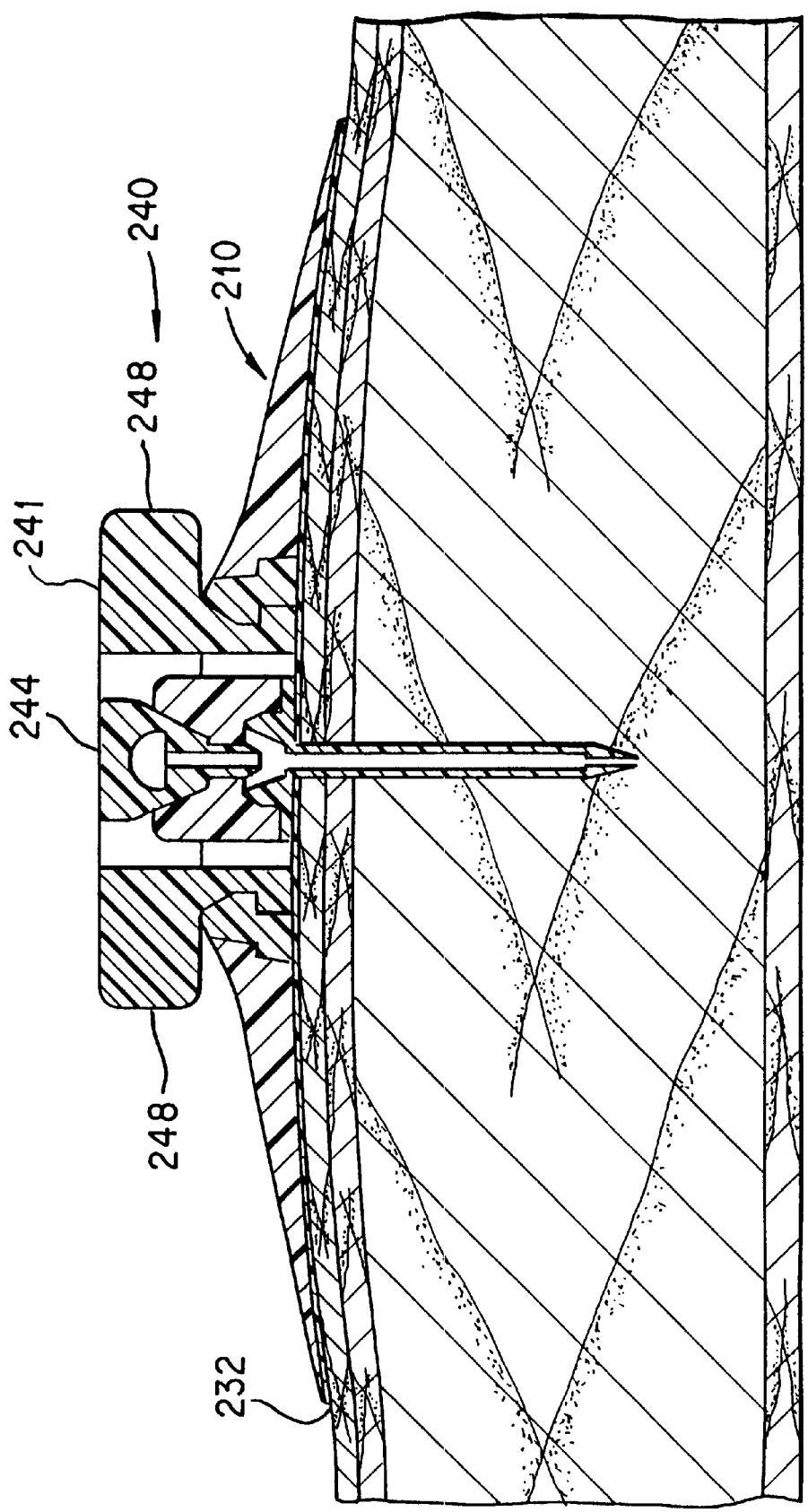
FIG. 16 is a cross section of the three-pronged connector shown attached to the injection port.

The cannula section 220 is best shown in FIGS. 11 and 12. The cannula section 220 consists of a flexible cannula 221 having a tapered entry section 222 located within a central section 223 that forms a pressure tight seal with the main body 210 just beneath the septum 205. An outer section 224 includes a lip 225 which is designed to engage a mating projection 247 of the three-pronged connector 240 as shown in FIGS. 15 and 16. The cannula section 220 also includes two tapered entry holes 226 which guide the tapered locking pins 246 of FIGS. 15 and 16 into the cannula section 220.

Adhesive assembly 230 consists of a two-sided adhesive sheet 232 which is joined on its inner surface to the underside of the main body 210, and on its outer side to two removable plastic sheets 234 which are separated by a diagonal cut 238 as shown by the dotted line in FIG. 10. When the tabs 236 which are part of the plastic sheets 234 are pulled away from the bottom surface of the main body 210, the outer adhesive surface of the adhesive sheet 232 is exposed and the injection port 200 can then be adhesively joined to the patient's skin, The projections 201 of the main body 210 are useful in pulling the injection port 200 off the skin.

Figure 14:
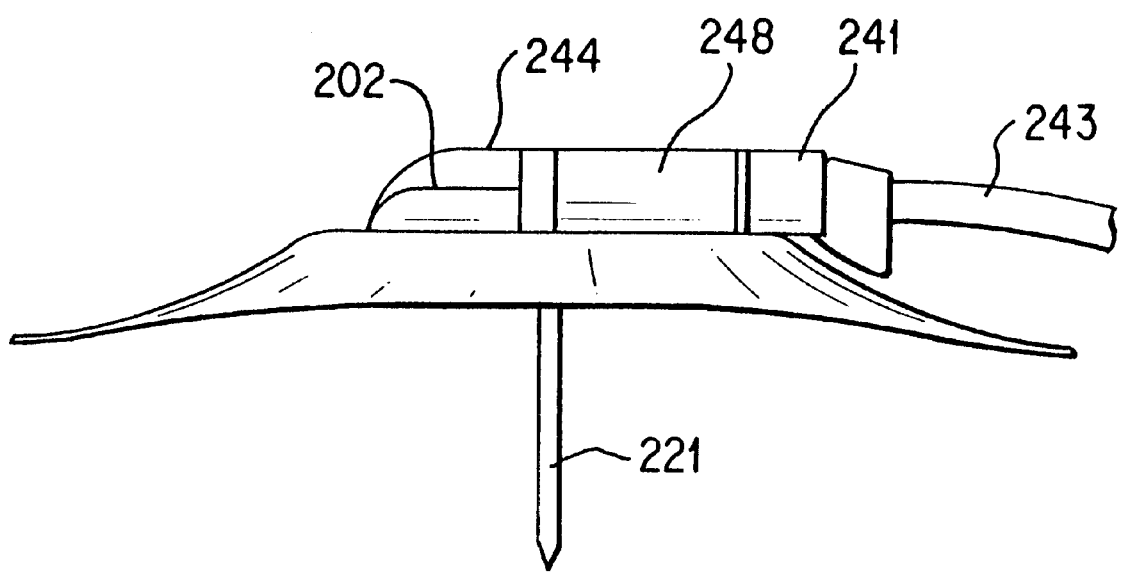
FIG. 14 is a side view of the connector and injection port.

FIGS. 13 and 14 illustrate the connector and tubing assembly 240 which has a three-pronged connector 241 mounted onto the main body 210 of the injection port 200. The assembly 240 consists of the connector 241 which is joined to a fluid connector 242 by means of tubing 243. The fluid connector 242 is typically a female Luer connector that is adapted to join to an external source of medication such as a portable insulin pump (not shown). The three-pronged connector 241 as illustrated in FIGS. 13, 14, 15 and 16 has a central prong 244 that is used to help guide the plastic needle 245 into the slit 204 of the septum 205 of the main body 210. The connector 241 is also guided into the tapered entry holes 226 of the main body 210 by means of the tapered locking pins 246 located on the outer two prongs of the three pronged connector 241. Thus, when the connector 241 is positioned just above the main body 210 as shown in FIG. 15, a downward finger pressure can be used to push the locking pins 246 into the tapered entry holes 226 as shown in FIGS. 15 and 16. When this is accomplished, the lip 225 of the cannula section 220 is locked onto the mating lip 247 of the locking pins 246. To remove the connector 241 from the cannula section 220, the patient uses his thumb and forefinger to squeeze together the outer surfaces 248 of the outer prongs of the connector 241. When this is done, the lips 225 and 247 disengage, and the connector 241 can be pulled out of the cannula section 220.

If the connector 241 is placed on a flat surface such as a table after it is pulled out of the cannula section 220, it will be noted that the plastic needle 245 will not touch the table surface. Thus the sterility of the plastic needle 245 can be maintained without placing a special cap over it. Furthermore, the flat upper surface of the septum 205 can be wiped with an alcohol swab before reinserting the plastic needle 245, thus assuring a sterile connection of the three-pronged connector 240 and precluding the need for a special sterility maintaining cover to be placed over the septum 205 when the connector 241 is removed from the cannula section 220. It should also be understood that the priming can be accomplished by attaching the connector 242 to a source of medication and pumping the medication through the tube 243 and then out the central lumen 249 of the plastic needle 245. The connector 241 can then be joined into the cannula section 220.

Figure 17:
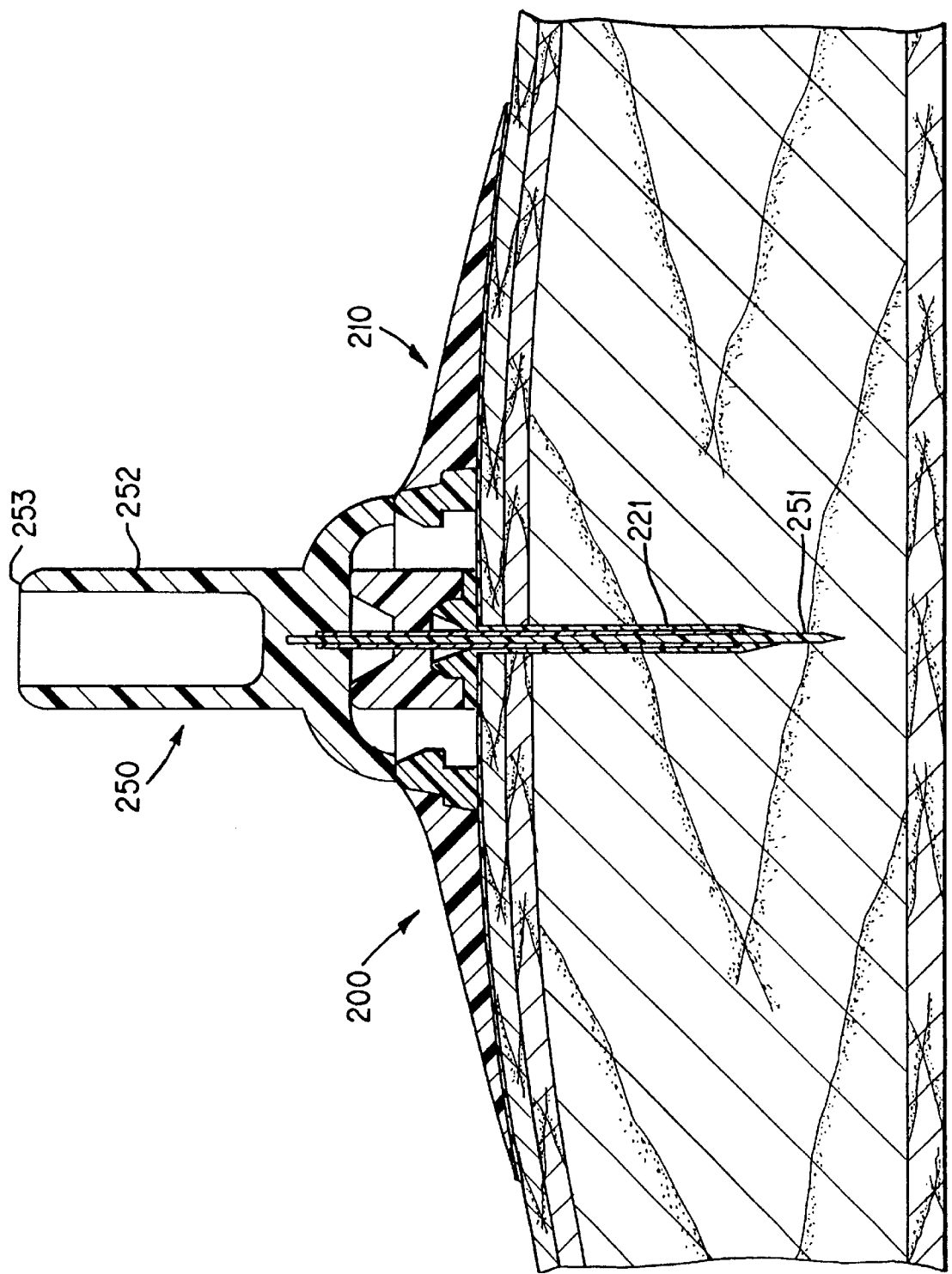
FIG. 17 is a cross section of the needle assembly and injection port showing the needle assembly as it is used to place the cannula through the skin and into the subcutaneous fat.

FIG. 17 illustrates a needle assembly 250 that is used to subcutaneously place the cannula 221 of the injection port 200. The needle assembly 250 consists of pointed needle 251 placed inside the cannula 221. The needle 251 is joined at its proximal end to a hollow handle 252. The shape of the proximal end 253 of the needle handle 252 as shown in FIG. 17 is ideal for secure placement of a finger tip when pushing the needle 251 and cannula 221 through the skin. After this is accomplished, the main body 210 is pushed firmly against the skin thus assuring a good adhesive connection of the injection part 200 onto the skin. The needle assembly 250 is then removed and the connector 241 is inserted into the cannula section 220 as illustrated in FIGS. 13, 14, 15 and 16.

The material of the main body 210 would be a low durometer elastomer such as silicone rubber, polyurethane or polyethylene. The cannula section would be molded from a similar elastomer material but of a considerably higher durometer. The connectors 241 and 242 and the needle handle 252 would be molded from a hard plastic such as polycarbonate. The main body 210 would be between 2 and 5 cm in diameter with all other dimensions being approximately as scaled from the drawings of FIGS. 10 to 17 inclusive.

Figure 18:
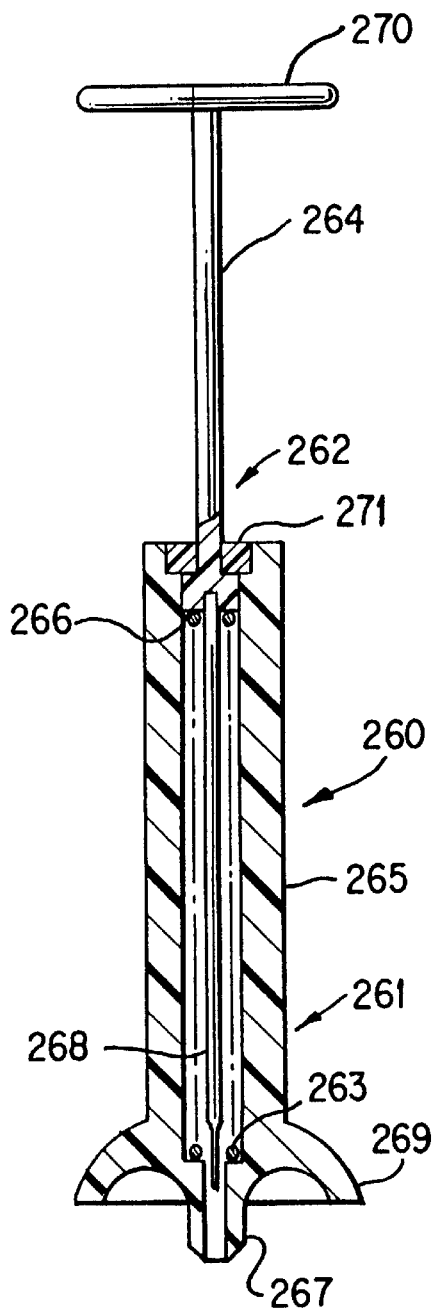
FIG. 18 is a cross section of a needle assembly that automatically shields the needle point with the needle shown in its retracted position.
Figure 19:
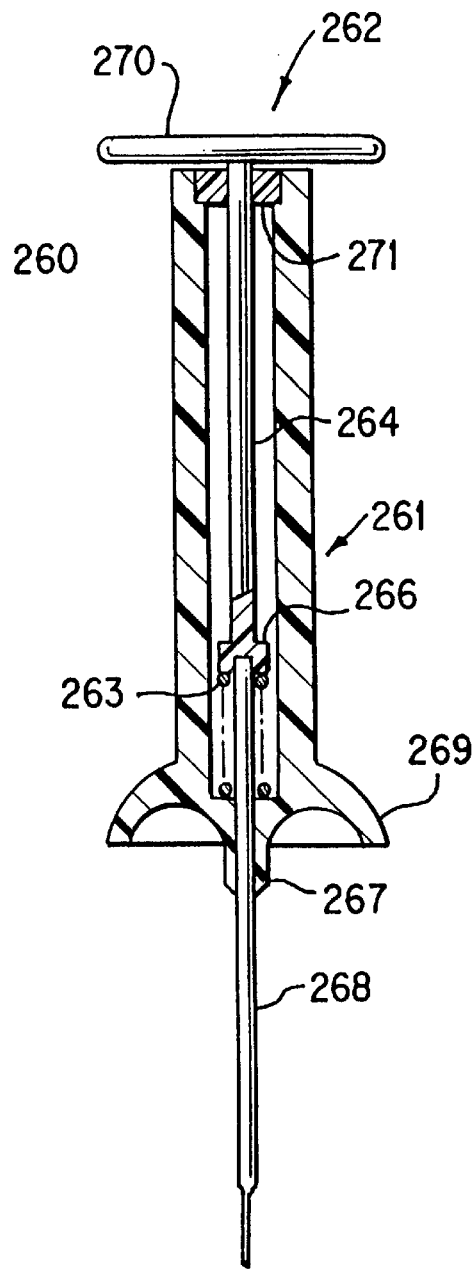
FIG. 19 is a cross section of a needle assembly that automatically shields the needle point with the needle shown in its extended position for inserting the injection port cannula through the skin.

FIGS. 18 and 19 show another embodiment of a needle assembly 260 that is designed to avoid inadvertent needle sticks by the patient or health care worker who places the injection port assembly onto the patient. The needle assembly 260 consists of a housing 261, slideable needle 262 and a compressional coil spring 263. The housing 261 consists of a body 265, a plastic needle 267, a distal end section 269 and a bushing 271. The slideable needle 262 consists of a shaft 264, a needle stop 266, a metal needle 268 and a finger push button 270.

The patient would receive an injection port assembly with the plastic needle 267 placed into the septum of the main body of the injection port and with the distal end section 269 in contact with the top of the main body. The spring 263 normally urges the slideable needle 262 to be in the position shown in FIG. 18. The patient would then hold the body 265 between his thumb and middle finger and use his index finger to apply a force to the finger push button 270 thus causing the slideable needle 262 to assume the position shown in FIG. 19. In that position, the needle 268 (which would be located within a flexible cannula) would be used to place the distal end of the flexible cannula through the skin and into the subcutaneous fat. The injection port assembly would then adhere to the skin, the needle assembly 260 would be pulled out, and the slideable needle 262 would automatically be placed into the position shown in FIG. 18. Thus, the sharpened point of the needle 268 would be shielded by the housing 261 thereby precluding inadvertent needle sticks. The needle assembly 260 would then be disposed of in the safe, needle retracted position shown in FIG. 18.

It is envisioned that a variety of other designs for safety needles could be used for placement of injection ports; the common feature being that the shapened needle point is retracted into a plastic needle housing.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. An injection port for delivery of medication from an external source through a patient's skin comprising:
   a generally flat, disk shaped main body formed from a single molded elastomer including a septum formed integral at the center of the main body; and,
   a cannula section formed from a single molded elastomer of a harder durometer as compared to the elastomer of the main body, the cannula section being joined with a pressure tight seal to the main body, the cannula section further having a flexible elongated cannula that protrudes in a generally downward direction from the main body.

2. The device of claim 1 wherein the septum that is formed integral with the main body has a slit to facilitate the passage of a plastic needle.

3. The device of claim 2 wherein guide ridges are situated around the septum to facilitate the placement of a plastic needle through the slit in the septum.

4. The device of claim 1 wherein the cannula section has two through holes each hole having an engagement means for engaging a releasable connector engagement means.

5. The device of claim 1 wherein both the upper and lower surfaces of the main body are generally of a concave shape.

6. The device of claim 1 wherein a pressure sensitive adhesive is applied to the bottom surface of the main body.

7. A device for delivery of medication from an external source through a patient's skin comprising:
   an injection port assembly having top and bottom surfaces, a main body, an adhesive section and an elongated cannula with a central lumen that protrudes from the bottom surface of the injection port assembly in a direction that is generally perpendicular to the bottom surface of the injection port assembly, the lumen having proximal and distal ends, the lumen's proximal end being situated just below a septum that is formed integral with and at the center of the main body, the injection port assembly further including two holes each including an engaging means for attachment to a fluid connector engaging means.

8. The device of claim 7 wherein the fluid connector has three prongs, the central prong having a passageway for medication and the outer two prongs having said fluid connector engaging means for releasable attachment to the cannula section engaging means.

9. The device of claim 8 wherein the central prong terminates in the plastic needle having a tapered distal end that is adapted to pass through a slit in the septum formed at the center of the main body, the plastic needle having a central lumen which is in fluid communication with the proximal end of cannula lumen after the plastic needle is inserted through the septum of the main body.

10. A device for delivery of medication from an external source through a patient's skin comprising:
    an injection port assembly having top and bottom surfaces, a main body, an adhesive section and an elongated cannula with a central lumen that protrudes from the bottom surface of the injection port assembly in a direction that is generally perpendicular to the bottom surface of the injection port assembly; and
    a needle assembly including a housing and a slideable metal needle that can be advanced into and through the cannula for subcutaneous insertion of the cannula, the slideable metal needle having a sharpened needle point at its distal end that is adapted to be withdrawn into the housing so that the sharpened needle point becomes completely shielded by the housing.

11. A device for delivery of medication from an external source through a patient's skin, comprising:
    an injection port assembly having a top surface, a bottom surface, a main body and an elongated cannula that protrudes in a direction that is generally perpendicular to the bottom surface of the injection port assembly, the injection port assembly also having fluid connection means located within the main body of the injection port assembly; and
    a connector and tubing assembly consisting of an elongated tube having a first end and a second end and having a first fluid connector located at the first end and a second fluid connector at the second end, the first fluid connector being adapted to be removably connected through the top surface of the injection port assembly and into the fluid connection means located within the main body of the injection port assembly.

12. The injection port assembly of claim 11 wherein an adhesive assembly consisting of an adhesive sheet that is covered by at least one removable plastic sheet is placed at the bottom surface of the injection port assembly.

13. The injection port assembly of claim 11 wherein the second fluid connector is adapted to join to an external source of medication.

14. The injection port assembly of claim 13 wherein the external source of medication is a portable insulin pump.

* * * * *